United States Patent
Yamane et al.

(10) Patent No.: US 6,518,435 B1
(45) Date of Patent: Feb. 11, 2003

(54) PROCESS FOR THE PREPARATION OF OXYIMINOALKANOIC ACID DERIVATIVES

(75) Inventors: Taihei Yamane, Takarazuka (JP); Atsushi Inagaki, Ikeda (JP); Osamu Yabe, Nishinomiya (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/111,480

(22) PCT Filed: Oct. 26, 2000

(86) PCT No.: PCT/JP00/07481

§ 371 (c)(1), (2), (4) Date: Apr. 25, 2002

(87) PCT Pub. No.: WO01/32608

PCT Pub. Date: May 10, 2001

(30) Foreign Application Priority Data

Oct. 29, 1999  (JP) ............................................. 11-308345

(51) Int. Cl.$^7$ ............................................. C07D 263/32
(52) U.S. Cl. ........................................ 548/236; 562/440
(58) Field of Search ........................... 548/236; 562/440

(56) References Cited

FOREIGN PATENT DOCUMENTS

| | | |
|---|---|---|
| JP | 08-176127 | 7/1996 |
| JP | 10-168071 | 6/1998 |
| WO | 96/02507 | 2/1996 |
| WO | 99/58510 | 11/1999 |

OTHER PUBLICATIONS

R. Plate et al., "A Biomimetic Approach to Sporidesmins. Synthesis of an α, β–epoxytryptophan Derivative", Tetrahedron, vol. 42, No. 33, pp. 6511–6518, 1986.

*Primary Examiner*—Robert W. Ramsuer
(74) *Attorney, Agent, or Firm*—Wenderoth, Lind & Ponack, L.L.P.

(57) ABSTRACT

The present invention provides, as an industrially advantageous production method, a method of producing a compound represented by the formula (III)

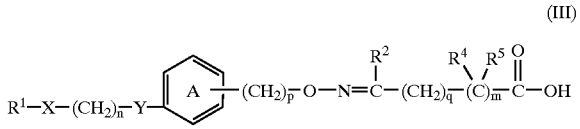

14 Claims, No Drawings

PROCESS FOR THE PREPARATION OF OXYIMINOALKANOIC ACID DERIVATIVES

This application is a 371 of PCT/JP00/07481 filed Oct. 26, 2000.

TECHNICAL FIELD

The present invention relates to a production method of oxyimino-alkanoic acid derivatives having an anti-diabetic activity.

BACKGROUND ART

As a production method of oxyimino-alkanoic acid derivatives involving arylmethylation of the oxime moiety of oxime alkanoic acid, JP-A-10-168071 and JP-A-8-176127 disclose production methods of thiazole acetic acid derivatives used as a side chain of cefem antibiotics. According to the Examples of these publications, potassium carbonate, sodium carbonate or lithium carbonate is used as a base for introducing triphenylmethyl into the oxime moiety by the reaction of an oxime alkanoic acid derivative with triphenylmethyl chloride.

As a production method of oxyimino-alkanoic acid amide derivatives involving arylmethylation of the oxime moiety of oxime alkanoic acid amide, Tetrahedron, vol. 42, p. 6511 (1986) discloses a production method of a synthetic intermediate for α,β-epoxytryptophan derivatives. According to this method, 1,2-dimethoxyethane is used as a solvent for the reaction of oxime alkanoic acid amide with benzyl bromide.

The present inventors found that, when a weak base, such as alkali metal carbonate and the like disclosed in the aforementioned publications, is used for producing a compound represented by the formula (III)

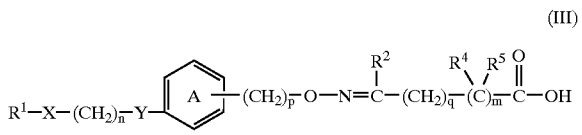

(III)

wherein $R^1$ is an optionally substituted hydrocarbon group or an optionally substituted heterocyclic group; X is a bond, —CO—, —CH(OH)— or —NR$^6$—($R^6$ is a hydrogen atom or an optionally substituted alkyl group); n is an integer of 1 to 3; Y is an oxygen atom, a sulfur atom, —SO—, —SO$_2$— or —NR$^7$—($R^7$ is a hydrogen atom or an optionally substituted alkyl group); ring A is a benzene ring optionally having 1 to 3 additional substituents; p is an integer of 1 to 8; $R^2$ is a hydrogen atom, an optionally substituted hydrocarbon group or an optionally substituted heterocyclic group; q is an integer of 0 to 6; m is 0 or 1; and $R^4$ and $R^5$ are the same or different and each is a hydrogen atom or an optionally substituted hydrocarbon group, or $R^4$ may be bonded to $R^2$ to form a ring, or a salt thereof, a by-product occurs to lower the yield of the objective oxyimino-alkanoic acid derivative, potentially contaminating the final product as a related substance. It was also clarified that the removal thereof requires further purification by separation using silica gel column chromatography and the like, making operation complicated, and may adversely affect the environment through the disposal of a large amount of waste silica gel and the like.

The present inventors also found that, when a low polar solvent such as 1,2-dimethoxyethane and the like disclosed in the aforementioned papers, is used for producing a compound represented by the formula (V)

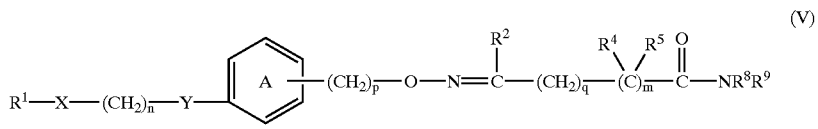

(V)

wherein $R^8$ and $R^9$ are the same or different and each is a hydrogen atom, an optionally substituted hydrocarbon group, an optionally substituted heterocyclic group or an optionally substituted acyl group, or $R^8$ and $R^9$ may be bonded to form a ring, and other symbols are as defined above, or a salt thereof, oxime alkanoic acid amide precipitates out in the reaction mixture as a metal salt, which significantly prevents progress of the reaction, lowers the reaction yield and causes residual starting materials. It was also clarified that, for removal of the residual starting materials, further purification by separation using silica gel chromatography and the like is necessary, which in turn makes operation complicated and possibly affects the environment adversely through the disposal of a large amount of waste silica gel and the like.

Under the circumstances, there is a strong demand for the development of an industrially advantageous and environmentally thoughtful production method of oxyimino-alkanoic acid derivatives, which can be put to use for practical production.

DISCLOSURE OF THE INVENTION

In an attempt to solve the above-mentioned problems, the present inventors have conducted intensive studies of an industrially advantageous production method of oxyimino-alkanoic acid derivatives, and found that the use of a metal alkoxide, which is a strong base, for the production of a compound represented by the above-mentioned formula (III) or a salt thereof by arylmethylation of the oxime moiety of oxime alkanoic acid suppresses formation of by-products. They have also found that the use of amides (polar solvents) as a reaction solvent for the production of oxyimino-alkanoic acid amide derivatives represented by the above-mentioned formula (V), by arylmethylation of the oxime moiety of oxime alkanoic acid amide increases reaction rates and decreases remaining starting material.

The present inventors have further developed the studies based on such findings, and, as a result, completed the present invention directed to a production method of oxyimino-alkanoic acid derivatives, which is an industrially advantageous and environmentally thoughtful production method that produces the derivatives having high quality in a high yield without purification by silica gel column chromatography.

Accordingly, the present invention provides
(1) a production method of a compound represented by the formula (III)

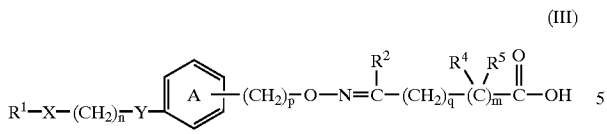

(III)

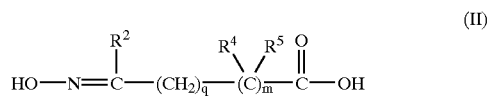

(II)

wherein

R¹ is an optionally substituted hydrocarbon group or an optionally substituted heterocyclic group;

X is a bond, —CO—, —CH(OH)— or —NR⁶—(R⁶ is a hydrogen atom or an optionally substituted alkyl group);

n is an integer of 1 to 3;

Y is an oxygen atom, a sulfur atom, —SO—, —SO₂— or —NR⁷—(R⁷ is a hydrogen atom or an optionally substituted alkyl group);

ring A is a benzene ring optionally having 1 to 3 additional substituents;

p is an integer of 1 to 8;

R² is a hydrogen atom or an optionally substituted hydrocarbon group or an optionally substituted heterocyclic group;

q is an integer of 0 to 6;

m is 0 or 1; and

R⁴ and R⁵ are the same or different and each is a hydrogen atom or an optionally substituted hydrocarbon group, or R may be bonded to R² to form a ring, or a salt thereof, which comprises reacting a compound represented by the formula (I)

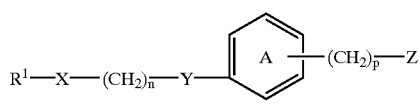

(I)

wherein Z is a halogen atom or OSO₂R¹⁰ (R¹⁰ is an alkyl group having 1 to 4 carbon atoms or an aryl group having 6 to 10 carbon atoms which is optionally substituted by alkyl group having 1 to 4 carbon atoms), and other symbols in the formula are as defined above, or a salt thereof, with a compound represented by the formula (II)

wherein the symbols in the formula are as defined above, or a salt thereof, in an amide in the presence of a metal alkoxide, (2) the production method of the above-mentioned (1), wherein the metal alkoxide is an alkali metal C₁₋₄ alkoxide, (3) the production method of the above-mentioned (2), wherein the alkali metal C₁₋₄ alkoxide is sodium tert-butoxide, (4) the production method of the above-mentioned (1), wherein the amide is N,N-dimethylacetamide, N,N-dimethylformamide, 1-methyl-2-pyrrolidone or 1,3-dimethyl-2-imidazolidinone, (5) the production method of the above-mentioned (4), wherein the amide is N,N-dimethylacetamide, (6) the production method of the above-mentioned (1), wherein the metal alkoxide is sodium tert-butoxide and the amide is N,N-dimethylacetamide, (7) the production method of the above-mentioned (1), wherein the compound represented by the formula (III) is (E)-4-[4-(5-methyl-2-phenyl-4-oxazolylmethoxy)benzyloxyimino]-4-phenylbutanoic acid or a salt thereof, (8) the production method of the above-mentioned (1), wherein the compound represented by the formula (III) is (E)-8-[4-(5-methyl-2-phenyl-4-oxazolylmethoxy)benzyloxyimino]-8-phenyloctanoic acid or a salt thereof, (9) a production method of a compound represented by the formula (V)

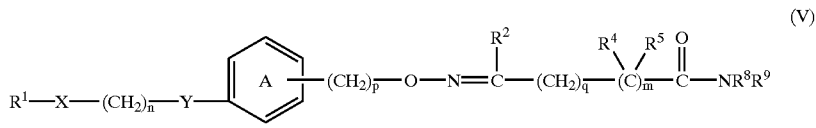

(V)

wherein R⁸ and R⁹ are the same or different and each is a hydrogen atom, an optionally substituted hydrocarbon group, an optionally substituted heterocyclic group or an optionally substituted acyl group, or R⁸ and R⁹ may be bonded to form a ring, and other symbols are as defined above, or a salt thereof, which comprises amidating the compound represented by the formula (III), which is produced according to the production method of (1) above, or a salt thereof,

(10) the production method of the above-mentioned (9), wherein the compound represented by the formula (V) is (E)-4-[4-(5-methyl-2-phenyl-4-oxazolylmethoxy)benzyloxyimino]-4-phenylbutylamide or a salt thereof,

(11) a production method of a compound represented by the formula (V)

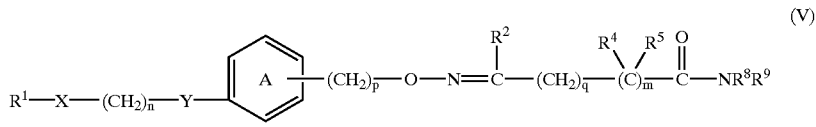

(V)

wherein R¹ is an optionally substituted hydrocarbon group or an optionally substituted heterocyclic group; X is a bond, —CO—, —CH(OH)— or —NR⁶—(R⁶ is a hydrogen atom or an optionally substituted alkyl group); n is an integer of 1 to 3; Y is an oxygen atom, a sulfur atom, —SO—, —SO₂— or —NR⁷—(R⁷ is a hydrogen atom or an optionally substituted alkyl group); ring A is a benzene ring optionally having 1 to 3 additional substituents; p is an integer of 1 to 8; R² is a hydrogen atom or an optionally substituted hydrocarbon group or an optionally substituted heterocyclic group; q is an integer of 0 to 6; m is 0 or 1; R⁸ and R⁹ are the same or different and each is a hydrogen atom, an optionally substituted hydrocarbon group, an optionally substituted heterocyclic group or an optionally substituted acyl group, or R⁸ and R⁹ may be bonded to form a ring; and R⁴ and R⁵ are the same or different and each is a hydrogen atom or an optionally substituted hydrocarbon group, or R⁴ may be bonded to R² to form a ring, or a salt thereof, which comprises reacting a compound represented by the formula (I)

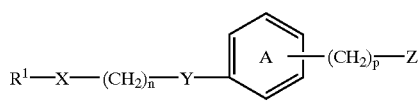

(I)

wherein Z is a halogen atom or OSO₂R¹⁰ (R¹⁰ is an alkyl group having 1 to 4 carbon atoms, an aryl group having 6 to 10 carbon atoms which is optionally substituted by alkyl group having 1 to 4 carbon atoms); and other symbols are as defined above, or a salt thereof, with a compound represented by the formula (IV)

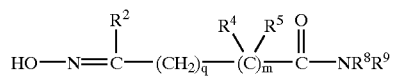

(IV)

wherein each symbol in the formula is as defined above, or a salt thereof, in an amide in the presence of a metal carbonate,

(12) the production method of the above-mentioned (11), wherein the metal carbonate is an alkali metal carbonate,

(13) the production method of the above-mentioned (11), wherein the amide is N,N-dimethylacetamide, N,N-dimethylformamide, 1-methyl-2-pyrrolidone or 1,3-dimethyl-2-imidazolidinone,

(14) the production method of the above-mentioned (11), wherein the compound represented by the formula (V) is (E)-4-[4-(5-methyl-2-phenyl-4-oxazolylmethoxy)benzyloxyimino]-4-phenylbutylamide or a salt thereof.

(1) Definition of R¹

As the hydrocarbon group of the "optionally substituted hydrocarbon group" represented by R¹ in the formulas, an aliphatic hydrocarbon group, an alicyclic hydrocarbon group, an alicyclic-aliphatic hydrocarbon group, an aromatic aliphatic hydrocarbon group and an aromatic hydrocarbon group are exemplified. These hydrocarbon groups preferably have 1 to 14 carbon atoms.

(1-1) Definition of Hydrocarbon Group for R¹

As the aliphatic hydrocarbon group, an aliphatic hydrocarbon group having 1 to 8 carbon atoms is preferable. As the aliphatic hydrocarbon group, for example, a saturated aliphatic hydrocarbon group having 1 to 8 carbon atoms (e.g., alkyl group and the like), such as methyl, ethyl, propyl, isopropyl, butyl, isobutyl, sec.-butyl, t.-butyl, pentyl, isopentyl, neopentyl, hexyl, isohexyl, heptyl, octyl and the like; and an unsaturated aliphatic hydrocarbon group having 2 to 8 carbon atoms (e.g., alkenyl group having 2 to 8 carbon atoms, alkadienyl group having 4 to 8 carbon atoms, alkenylalkynyl group having 2 to 8 carbon atoms, alkadiynyl group having 4 to 8 carbon atoms and the like), such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl and the like, are mentioned.

As the alicyclic hydrocarbon group, an alicyclic hydrocarbon group having 3 to 7 carbon atoms is preferable. As the alicyclic hydrocarbon group, for example, a saturated alicyclic hydrocarbon group having 3 to 7 carbon atoms (e.g., cycloalkyl group and the like), such as cyclopropyl, cyclobutyl, cyclopentyl, cyclohexyl, cycloheptyl and the like; and an unsaturated alicyclic hydrocarbon group having 5 to 7 carbon atoms (e.g., cycloalkenyl group, cycloalkadienyl group and the like), such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and the like, are mentioned.

As the alicyclic-aliphatic hydrocarbon group, the groups (e.g., cycloalkyl-alkyl group, cycloalkenyl-alkyl group and the like) are mentioned, wherein the above-mentioned alicyclic hydrocarbon group and an aliphatic hydrocarbon group are bonded. Of the alicyclic-aliphatic hydrocarbon groups, one having 4 to 9 carbon atoms is preferable. As the alicyclic-aliphatic hydrocarbon group, for example, cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and the like are mentioned.

As the aromatic aliphatic hydrocarbon group, an aromatic aliphatic hydrocarbon group having 7 to 13 carbon atoms (e.g., aralkyl group having 7 to 13 carbon atoms, arylalkenyl group having 8 to 13 carbon atoms, and the like) is preferable. As the aromatic aliphatic hydrocarbon group, for example, phenylalkyl having 7 to 9 carbon atoms such as benzyl, phenethyl, 1-phenylethyl, 1-phenylpropyl, 2-phenylpropyl, 3-phenylpropyl and the like; naphthylalkyl having 11 to 13 carbon atoms, such as α-naphthylmethyl, α-naphthylethyl, β-naphthylmethyl, β-naphthylethyl and the like; phenylalkenyl having 8 to 10 carbon atoms such as styryl and the like; and naphthylalkenyl having 12 or 13 carbon atoms such as 2-(2-naphthylvinyl) and the like are mentioned.

As the aromatic hydrocarbon group, an aromatic hydrocarbon group having 6 to 14 carbon atoms (e.g., aryl group and the like) is preferable. As the aromatic hydrocarbon group, for example, phenyl, naphthyl, anthryl, phenanthryl, acenaphthylenyl, biphenylyl and the like are mentioned. Of these, phenyl, 1-naphthyl, 2-naphthyl and the like are preferable.

(1-2) Definition of Heterocyclic Group for R¹

As the heterocyclic group of the "optionally substituted heterocyclic group" represented by R¹ in the formulas, a 5 to 7-membered monocyclic heterocyclic group or fused heterocyclic group, containing, as a ring-constituting atom besides carbon atom, 1 to 4 heteroatoms selected from oxygen atom, sulfur atom and nitrogen atom is mentioned. As the fused heterocycle, for example, a fused ring of these 5 to 7-membered monocyclic heterocycles with a 6-membered ring containing 1 or 2 nitrogen atoms, benzene ring or a 5-membered ring containing one sulfur atom is mentioned.

Specific examples of the heterocyclic group include aromatic heterocyclic groups, such as 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-5-yl, 1,3,4-oxadiazol-2-yl, 1,3,4-thiadiazol-2-yl, 1,2,4-triazol-1-yl, 1,2,4-triazol-3-yl, 1,2,3-triazol-1-yl, 1,2,3-triazol-2-yl, 1,2,3-triazol-4-yl, tetrazol-1-yl, tetrazol-5-yl, 2-quinolyl, 3-quinolyl, 4-quinolyl, 2-quinazolyl, 4-quinazolyl, 2-quinoxalyl, 2-benzoxazolyl, 2-benzothiazolyl, benzimidazol-1-yl, benzimidazol-2-yl, indol-1-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and the like; a non-aromatic heterocyclic group, such as 1-pyrrolidinyl, piperidino, morpholino, thiomorpholino, 1-piperazinyl, hexamethylenimin-1-yl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxothiazolidin-3-yl and the like; and the like are mentioned.

The heterocyclic group is preferably pyridyl, oxazolyl, thiazolyl, benzoxazolyl or benzothiazolyl.

(1-3) Definition of Substituent for Hydrocarbon Group and/or Heterocyclic Group for $R^1$ In the formulas, the hydrocarbon group and heterocyclic group represented by $R^1$ optionally have 1 to 5, preferably 1 to 3, substituents at substitutable positions. As the substituent, for example, optionally substituted aliphatic hydrocarbon group, optionally substituted alicyclic hydrocarbon group, optionally substituted aromatic hydrocarbon group, optionally substituted aromatic heterocyclic group, optionally substituted non-aromatic heterocyclic group, halogen atom, nitro group, optionally substituted amino group, optionally substituted acyl group, optionally substituted hydroxy group, optionally substituted thiol group, and optionally esterified or amidated carboxyl group are mentioned.

With respect to the "optionally substituted aliphatic hydrocarbon group", "optionally substituted alicyclic hydrocarbon group", "optionally substituted aromatic hydrocarbon group", "optionally substituted aromatic heterocyclic group" and "optionally substituted non-aromatic heterocyclic group", the substituent therefor is exemplified by $C_{1-6}$ alkyl group, $C_{1-6}$ alkoxy group, halogen atom (e.g., fluorine, chlorine, bromine, iodine and the like), nitro group, $C_{1-6}$ haloalkyl group and $C_{1-6}$ haloalkoxy group. The number of substituent is, for example, 1 to 3.

As the aliphatic hydrocarbon group, a linear or branched aliphatic hydrocarbon group having 1 to 15 carbon atoms, such as alkyl group, alkenyl group, alkynyl group and the like, are mentioned.

Preferable examples of the alkyl group include an alkyl group having 1 to 10 carbon atoms, such as methyl, ethyl, propyl, isopropyl, butyl, isobutyl, sec.-butyl, t.-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Preferable examples of the alkenyl group include an alkenyl group having 2 to 10 carbon atoms, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Preferable examples of the alkynyl group include an alkynyl group having 2 to 10 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

As the alicyclic hydrocarbon group, a saturated or unsaturated alicyclic hydrocarbon group having 3 to 12 carbon atoms, such as cycloalkyl group, cycloalkenyl group, cycloalkadienyl group and the like, are mentioned.

Preferable examples of the cycloalkyl group include a cycloalkyl group having 3 to 10 carbon atoms, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.]octyl, bicyclo[3.2.2]nonyl, bicyclo[3.3.1]nonyl, bicyclo[4.2.1]nonyl, bicyclo[4.3.1]decyl and the like.

Preferable examples of the cycloalkenyl group include a cycloalkenyl group having 3 to 10 carbon atoms, such as 2-cyclopenten-1-yl, 3-cyclopenten-1-yl, 2-cyclohexen-1-yl, 3-cyclohexen-1-yl and the like.

Preferable examples of the cycloalkadienyl group include a cycloalkadienyl group having 4 to 10 carbon atoms, such as 2,4-cyclopentadien-1-yl, 2,4-cyclohexadien-1-yl, 2,5-cyclohexadien-1-yl and the like.

Preferable examples of the aromatic hydrocarbon group include an aromatic hydrocarbon group having 6 to 14 carbon atoms (e.g., aryl group and the like), such as phenyl, naphthyl, anthryl, phenanthryl, acenaphthylenyl, biphenylyl and the like. Of these, phenyl, 1-naphthyl, 2-naphthyl and the like are preferable.

Preferable examples of the aromatic heterocyclic group include a 5 to 7-membered aromatic monocyclic heterocyclic group, containing, as a ring-constituting atom besides carbon atom, 1 to 4 heteroatoms selected from oxygen atom, sulfur atom and nitrogen atom, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl and the like; a bicyclic or tricyclic aromatic fused heterocycle having 3 to 13 carbon atoms, which contains, as a ring-constituting atom besides carbon atom, 1 to 5 heteroatoms selected from oxygen atom, sulfur atom and nitrogen atom, such as benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, α-carbonylyl, β-carbonylyl, γ-carbonylyl, acridinyl, phenoxazinyl, phenothiazinyl, phenazinyl, phenoxathiinyl, thianthrenyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like; and the like.

Preferable examples of the non-aromatic heterocyclic group include those having 2 to 10 carbon atoms, which contain, as a ring-constituting atom besides carbon atom, 1 to 3 heteroatoms selected from oxygen atom, sulfur atom and nitrogen atom, such as oxiranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, thiomorpholino and the like.

Examples of the halogen atom include fluorine, chlorine, bromine and iodine, with preference given to fluorine and chlorine.

As the optionally substituted amino group, for example, an amino group optionally mono- or di-substituted by an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms, an acyl group having 1 to 13 carbon atoms (e.g., alkanoyl group having 2 to 10 carbon atoms, arylcarbonyl group having 7 to 13 carbon atoms and the like) or aryl group having 6 to 12 carbon atoms is mentioned. The acyl group here is the same as the acyl group of the "optionally substituted acyl group" to be mentioned below.

As the substituted amino group, for example, methylamino, dimethylamino, ethylamino, diethylamino, propylamino, dibutylamino, diallylamino, cyclohexylamino, acetylamino, propionylamino, benzoylamino, phenylamino, N-methyl-N-phenylamino and the like are mentioned.

The acyl group of the optionally substituted acyl group includes, for example, an acyl group having 1 to 13 carbon atoms, such as formyl, and a group wherein alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms, an aryl group having 6 to 12 carbon atoms or an aromatic heterocyclic group (e.g., thienyl, furyl, pyridyl and the like) is bonded to a carbonyl group, and the like.

Preferable examples of acyl group include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, isonicotinoyl and the like.

The acyl group may have 1 to 3 substituents at substitutable positions. Examples of the substituent include alkyl group having 1 to 3 carbon atoms, such as alkoxy group having 1 to 3 carbon atoms, halogen (e.g., fluorine, chlorine, iodine and the like), nitro, hydroxy, amino and the like.

The acyl group in a different form is represented by the following formula

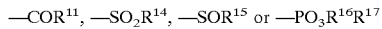
—COR$^{11}$, —SO$_2$R$^{14}$, —SOR$^{15}$ or —PO$_3$R$^{16}$R$^{17}$ wherein R$^{11}$, R$^{14}$, R$^{15}$, R$^{16}$ and R$^{17}$ are the same or different and each is an optionally substituted hydrocarbon group.

Examples of the hydrocarbon group of the "optionally substituted hydrocarbon group" represented by R$^{11}$, R$^{14}$, R$^{15}$, R$^{16}$ and R$^{17}$ include an alkyl group having 1 to 10 carbon atoms, a cycloalkyl group having 3 to 10 carbon atoms, an alkenyl group having 2 to 10 carbon atoms, a cycloalkenyl group having 3 to 10 carbon atoms and an aryl group having 6 to 12 carbon atoms. Examples of the substituent of the "optionally substituted hydrocarbon group" include C$_{1-6}$ alkyl group (except that wherein the hydrocarbon group is an alkyl group), C$_{1-6}$ alkoxy group, halogen atom (e.g., fluorine, chlorine, bromine, iodine and the like), nitro group, C$_{1-6}$ haloalkyl group and C$_{1-6}$ haloalkoxy group. The number of substituent is, for example, 1 to 3.

In the optionally substituted hydroxy group, the substituted hydroxy group is exemplified by an optionally substituted alkoxy group, an optionally substituted alkenyloxy group, an optionally substituted aralkyloxy group, an optionally substituted acyloxy group, an optionally substituted aryloxy group and the like.

Preferable examples of the alkoxy group include an alkoxy group having 1 to 10 carbon atoms, such as methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy, cyclobutoxy, cyclopentyloxy, cyclohexyloxy and the like.

Preferable examples of the alkenyloxy group include an alkenyloxy group having 2 to 10 carbon atoms, such as allyloxy, crotyloxy, 2-pentenyloxy, 3-hexenyloxy, 2-cyclopentenylmethoxy, 2-cyclohexenylmethoxy and the like.

Preferable examples of the aralkyloxy group include an aralkyloxy group having 7 to 10 carbon atoms, such as phenyl-C1–4 alkyloxy (e.g., benzyloxy, phenethyloxy and the like) and the like.

Preferable examples of the acyloxy group include an acyloxy group having 2 to 13 carbon atoms, more preferably alkanoyloxy having 2 to 4 carbon atoms (e.g., acetyloxy, propionyloxy, butyryloxy, isobutyryloxy and the like) and the like.

Preferable examples of the aryloxy group include an aryloxy group having 6 to 14 carbon atoms, such as phenoxy, naphthyloxy and the like.

The above-mentioned alkoxy group, alkenyloxy group, aralkyloxy group, acyloxy group and aryloxy group may have 1 or 2 substituents at substitutable positions. Examples of such substituent include halogen (e.g., fluorine, chlorine, bromine and the like), alkoxy group having 1 to 3 carbon atoms and the like. As the substituted aryloxy group, for example, 4-chlorophenoxy, 2-methoxyphenoxy and the like are mentioned.

In the optionally substituted thiol group, the substituted thiol group includes, for example, alkylthio, cycloalkylthio, aralkylthio, acylthio, arylthio, heteroarylthio and the like.

Preferable examples of the alkylthio group include an alkylthio group having 1 to 10 carbon atoms, such as methylthio, ethylthio, propylthio, isopropylthio, butylthio, isobutylthio, sec.-butylthio, t.-butylthio, pentylthio, isopentylthio, neopentylthio, hexylthio, heptylthio, nonylthio and the like.

Preferable examples of the cycloalkylthio group include a cycloalkylthio group having 3 to 10 carbon atoms, such as cyclobutylthio, cyclopentylthio, cyclohexylthio and the like.

Preferable examples of the aralkylthio group include an aralkylthio group having 7 to 10 carbon atoms, such as phenyl-C1–4 alkylthio (e.g., benzylthio, phenethylthio and the like) and the like.

Preferable examples of the acylthio group include an acylthio group having 2 to 13 carbon atoms, more preferably an alkanoylthio group having 2 to 4 carbon atoms (e.g., acetylthio, propionylthio, butyrylthio, isobutyrylthio and the like) and the like.

Preferable examples of the arylthio group include an arylthio group having 6 to 14 carbon atoms, such as phenylthio, naphthylthio and the like.

Preferable examples of the heteroarylthio group include, in addition to 2-pyridylthio, 3-pyridylthio and the like, 2-imidazolylthio, 1,2,4-triazol-5-ylthio and the like.

In the optionally esterified carboxyl group, the esterified carboxyl group is, for example, alkoxycarbonyl group having 2 to 5 carbon atoms (e.g., methoxycarbonyl, ethoxycarbonyl, propoxycarbonyl, butoxycarbonyl and the like), aralkyloxycarbonyl group having 8 to 10 carbon atoms (e.g., benzyloxycarbonyl and the like), aryloxycarbonyl group having 7 to 15 carbon atoms (e.g., phenoxycarbonyl, p-tolyloxycarbonyl and the like) which is optionally substituted by 1 or 2 alkyl groups having 1 to 3 carbon atoms, and the like.

In the optionally amidated carboxyl group, the amidated carboxyl group is, for example, a group represented by the formula:

—CON($R^{12}$)($R^{13}$)

wherein $R^{12}$ and $R^{13}$ are the same or different and each is hydrogen atom, optionally substituted hydrocarbon group or optionally substituted heterocyclic group.

As used herein, the hydrocarbon group of the "optionally substituted hydrocarbon group" represented by $R^{12}$ and $R^{13}$ and the heterocyclic group of the "optionally substituted heterocyclic group" represented by $R^{12}$ and $R^{13}$ are each exemplified by aliphatic hydrocarbon group, alicyclic hydrocarbon group, aromatic hydrocarbon group and heterocyclic group, which have been exemplified above for the "hydrocarbon group of the "optionally substituted hydrocarbon group" represented by $R^1$" and the "heterocyclic group of the "optionally substituted heterocyclic group" represented by $R^1$". The hydrocarbon group and heterocyclic group may have 1 to 3 substituents at substitutable positions. Examples of such substituent include halogen (e.g., fluorine, chlorine, bromine, iodine and the like), alkyl group having 1 to 4 carbon atoms, alkoxy group having 1 to 4 carbon atoms and the like.

In the formulas, the substituent of the hydrocarbon group and heterocyclic group represented by $R^1$ is preferably an alkyl group having 1 to 10 carbon atoms, an aromatic heterocyclic group and an aryl group having 6 to 14 carbon atoms. More preferably, it is alkyl having 1 to 3 carbon atoms, furyl, thienyl, phenyl or naphthyl.

When the substituent of the hydrocarbon group and heterocyclic group represented by $R^1$ is alicyclic hydrocarbon group, aromatic hydrocarbon group, aromatic heterocyclic group or non-aromatic heterocyclic group, it may additionally have one or more, preferably 1 to 3, substituents. Examples of such substituent include, for example, alkyl group having 1 to 6 carbon atoms, alkenyl group having 2 to 6 carbon atoms, cycloalkyl group having 3 to 10 carbon atoms, aryl group having 6 to 14 carbon atoms (e.g., phenyl, naphthyl and the like), aromatic heterocyclic group (e.g., thienyl, furyl, pyridyl, oxazolyl, thiazolyl and the like), non-aromatic heterocyclic group (e.g., tetrahydrofuryl, morpholino, thiomorpholino, piperidino, pyrrolidinyl, piperazinyl and the like), aralkyl group having 7 to 9 carbon atoms, amino group, amino group mono- or di-substituted by alkyl group having 1 to 4 carbon atoms or acyl group having 2 to 8 carbon atoms (e.g., alkanoyl group and the like), amidino group, acyl group having 2 to 8 carbon atoms (e.g., alkanoyl group and the like), carbamoyl group, carbamoyl group mono- or di-substituted by alkyl group having 1 to 4 carbon atoms, sulfamoyl group, sulfamoyl group mono- or di-substituted by alkyl group having 1 to 4 carbon atoms, carboxyl group, alkoxycarbonyl group having 2 to 8 carbon atoms, hydroxy group, alkoxy group having 1 to 6 carbon atoms, alkenyloxy group having 2 to 5 carbon atoms, cycloalkyloxy group having 3 to 7 carbon atoms, aralkyloxy group having 7 to 9 carbon atoms, aryloxy group having 6 to 14 carbon atoms (e.g., phenyloxy, naphthyloxy and the like), thiol group, alkylthio group having 1 to 6 carbon atoms, aralkylthio group having 7 to 9 carbon atoms, arylthio group having 6 to 14 carbon atoms (e.g., phenylthio, naphthylthio and the like), sulfo group, cyano group, azido group, nitro group, nitroso group, halogen atom (e.g., fluorine, chlorine, bromine, iodine and the like).

(1-4) Preferable Examples of $R^1$

In the formulas, $R^1$ is preferably an optionally substituted heterocyclic group, more preferably an optionally substituted pyridyl, an optionally substituted oxazolyl, an optionally substituted thiazolyl or an optionally substituted triazolyl. $R^1$ is particularly preferably pyridyl, oxazolyl, thiazolyl or triazolyl, each of which optionally having 1 or 2 substituents selected from alkyl having 1 to 3 carbon atoms, cycloalkyl having 3 to 7 carbon atoms, furyl, thienyl, phenyl and naphthyl. As used herein, furyl, thienyl, phenyl and naphthyl may have 1 or 2 substituents selected from alkyl having 1 to 3 carbon atoms, alkoxy having 1 to 3 carbon atoms, halogen (e.g., fluorine, chlorine, bromine, iodine and the like) and haloalkyl having 1 to 3 carbon atoms.

Preferable examples of $R^1$ include an optionally substituted heterocyclic group and an optionally substituted cyclic hydrocarbon group, which are represented by the following formulas:

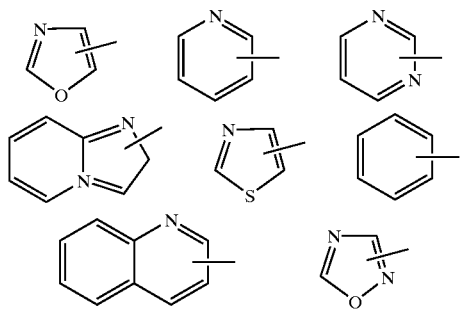

These groups may have 1 or 2 substituents selected from phenyl, furyl, thienyl and alkyl having 1 to 4 carbon atoms. The phenyl, furyl and thienyl may have 1 or 2 substituents selected from alkyl having 1 to 6 carbon atoms, alkoxy having 1 to 6 carbon atoms, halogen (e.g., fluorine, chlorine, bromine, iodine and the like), nitro, haloalkyl having 1 to 6 carbon atoms and haloalkoxy having 1 to 6 carbon atoms. The alkyl having 1 to 4 carbon atoms may have 1 or 2 substituents selected from alkoxy having 1 to 6 carbon atoms, halogen (e.g., fluorine, chlorine, bromine, iodine and the like), nitro, haloalkyl having 1 to 6 carbon atoms and haloalkoxy having 1 to 6 carbon atoms.

$R^1$ is more preferably a group represented by the following formula:

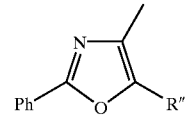

wherein Ph is an optionally substituted phenyl group and R" is a hydrogen atom or an optionally substituted alkyl group having 1 to 6 carbon atoms.

The substituent for the phenyl group represented by Ph and the alkyl group having 1 to 6 carbon atoms represented by R" is, for example, alkoxy having 1 to 6 carbon atoms, halogen (e.g., fluorine, chlorine, bromine, iodine and the like), nitro, haloalkyl having 1 to 6 carbon atoms or haloalkoxy having 1 to 6 carbon atoms. The number of substituent is, for example, 1 to 3.

(2) Definition of X

In the formulas, X is a bond or a group represented by —CO—, —CH(OH)— or —$NR^6$—($R^6$ is hydrogen atom or optionally substituted alkyl group), of which a bond, —CH (OH)— and —NR⁶— are preferable, and a bond and —NR⁶— are more preferable.

As used herein, as the alkyl group of the "optionally substituted alkyl group" represented by $R^6$, an alkyl group having 1 to 4 carbon atoms, such as methyl, ethyl, propyl, isopropyl, butyl, isobutyl, sec.-butyl, t.-butyl and the like, is mentioned. The alkyl group may have 1 to 3 substituents at substitutable positions and examples of such substituent include halogen (e.g., fluorine, chlorine, bromine, iodine), alkoxy group having 1 to 4 carbon atoms (e.g., methoxy, ethoxy, propoxy, isopropoxy, butoxy, isobutoxy, sec.-butoxy, t.-butoxy and the like), hydroxy group, nitro group and acyl group having 1 to 4 carbon atoms (e.g., alkanoyl group having 1 to 4 carbon atoms such as formyl, acetyl, propionyl and the like).

(3) Definition of n and Y

In the formulas, n is an integer of 1 to 3, preferably 1 or 2.

In the formulas, Y is —O—, —S—, —SO—, —SO2— or —NR⁷—($R^7$ is hydrogen atom or optionally substituted alkyl group), of which —O—, —S— and —NR⁷— are preferable. As used herein, the "optionally substituted alkyl group" represented by $R^7$ is exemplified by those recited as the above-mentioned "optionally substituted alkyl group" represented by $R^6$.

(4) Definition of Ring A

In the formulas, ring A is a benzene ring, and the benzene ring optionally has 1 to 3 substituents at substitutable positions. Examples of such substituent include alkyl group, optionally substituted hydroxy group, halogen atom, optionally substituted acyl group, nitro group and optionally substituted amino group, all of which are exemplified by those recited as the substituent for hydrocarbon group and heterocyclic group represented by $R^1$.

Said substituent is preferably an alkyl group having 1 to 4 carbon atoms, an alkoxy group having 1 to 4 carbon atoms or a halogen atom.

In the formulas, the partial structural formula

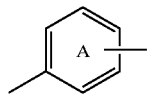

is preferably or

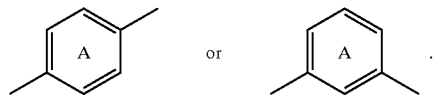

(5) Definition of p

In the formulas, p is an integer of 1 to 8, preferably an integer of 1 to 3.

(6) Definition of $R^2$

In the formulas, the "optionally substituted hydrocarbon group" represented by $R^2$ is exemplified by those recited as the "optionally substituted hydrocarbon group" represented by $R^1$.

The "optionally substituted heterocyclic group" represented by $R^2$ is exemplified by those recited as the "optionally substituted heterocyclic group" represented by $R^1$.

In the formulas, $R^2$ is preferably an optionally substituted hydrocarbon group. $R^2$ is more preferably an optionally substituted aliphatic hydrocarbon group, an optionally substituted alicyclic hydrocarbon group, an optionally substituted aromatic aliphatic hydrocarbon group or an optionally substituted aromatic hydrocarbon group, particularly preferably an optionally substituted alkyl having 1 to 4 carbon atoms, an optionally substituted phenylalkenyl group having 8 to 10 carbon atoms or an optionally substituted aryl group having 6 to 14 carbon atoms.

The substituent that these hydrocarbon groups may have is preferably halogen atom, alkoxy group having 1 to 4 carbon atoms, aryloxy group having 6 to 14 carbon atoms and aromatic heterocyclic group (e.g., furyl, thienyl). The number of substituent is, for example, 1 to 3.

(7) Definition of q and m

In the formulas, q is an integer of 0 to 6, preferably 0 to 4. m is 0 or 1.

(8) Definition of $R^8$ and $R^9$

In the formulas, $R^8$ and $R^9$ are the same or different and each is a hydrogen atom, an optionally substituted hydrocarbon group, an optionally substituted heterocyclic group, or an optionally substituted acyl group, or $R^8$ and $R^9$ may be bonded to form a ring.

The "optionally substituted hydrocarbon group" and "optionally substituted heterocyclic group" represented by $R^8$ and $R^9$ are each exemplified by those recited as the "optionally substituted hydrocarbon group" and "optionally substituted heterocyclic group" represented by $R^1$.

The "optionally substituted acyl group" represented by $R^8$ and $R^9$ are exemplified by those similar to the "optionally substituted acyl group" recited as the substituent that the "optionally substituted hydrocarbon group" represented by $R^1$ may have.

$R^8$ and $R^9$ may be bonded to form a 5 to 7-membered cyclic amino group. Concrete examples of cyclic amino group include 1-pyrrolidinyl, 1-piperidinyl, 1-hexamethyleneiminyl, 4-morpholino, 4-thiomorpholino and the like.

(9) Definition of $R^4$ and $R^5$

In the formulas, $R^4$ and $R^5$ are the same or different and each is a hydrogen atom or an optionally substituted hydrocarbon group, or $R^4$ may be bonded to $R^2$ to form a ring.

The "optionally substituted hydrocarbon group" represented by $R^4$ and $R^5$ is exemplified by those similar to the aforementioned "optionally substituted hydrocarbon group" of $R^1$, with preference given to those similar to the aforementioned "optionally substituted alkyl group" represented by $R^6$ and the like.

$R^4$ may be bonded to $R^2$ to form a ring. The ring formed by $R^4$ and $R^2$ in combination is, for example, cycloalkane having 5 to 11 carbon atoms, cycloalkene having 5 to 11 carbon atoms and the like, which are specifically cyclopentane, cyclopentene, cyclohexane, cyclohexene, cycloheptane, cycloheptene, cyclooctane, cyclooctene, cyclononane, cyclononene, cyclodecane, cyclodecene, cycloundecane and cycloundecene and the like.

(10) Definition of Z

In the formulas, Z is a halogen atom or $OSO_2R^{10}$ ($R^{10}$ is alkyl group having 1 to 4 carbon atoms, aryl group having 6 to 10 carbon atoms that is optionally substituted by alkyl group having 1 to 4 carbon atoms).

As the halogen atom, fluorine, chlorine, bromine and the like are mentioned, with preference given to chlorine.

With regard to the "alkyl having 1 to 4 carbon atoms" and "an aryl group having 6 to 10 carbon atoms that is optionally substituted by alkyl group having 1 to 4 carbon atoms" represented by $R^{10}$, the "alkyl having 1 to 4 carbon atoms" is exemplified by those mentioned above which are recited as $R^6$. The aryl group having 6 to 10 carbon atoms of the "aryl group having 6 to 10 carbon atoms that is optionally substituted by alkyl group having 1 to 4 carbon atoms" is exemplified by phenyl, naphthyl and the like, with preference given to phenyl.

Preferable examples of Z include chlorine, methanesulfonyl, toluenesulfonyl and the like, with preference given to chlorine.

(11) (E) Form and/or (Z) Form Compound

The compounds represented by the formulas (II) and (III) have an (E) form and a (Z) form at imino bond. The compound includes such (E) form and (Z) form as single compounds, and a mixture thereof.

(12) Preferable Examples

Preferable compounds represented by the formulas (III) and (V), which are produced according to the production method of the present invention, include the following compounds:

(1) (E)-4-[4-(5-methyl-2-phenyl-4-oxazolylmethoxy)-benzyloxyimino]-4-phenylbutanoic acid or a salt thereof,
(2) (E)-8-[4-(5-methyl-2-phenyl-4-oxazolylmethoxy)-benzyloxyimino]-8-phenyloctanoic acid or a salt thereof,
(3) (E)-4-[4-(5-methyl-2-phenyl-4-oxazolylmethoxy)-benzyloxyimino]-4-phenylbutylamide or a salt thereof.

The salt of the compound represented by the formula (I), (II), (III), (IV) or (V) (hereinafter sometimes to be briefly referred to as compound (I), (II), (III), (IV) or (V)) is preferably a pharmacologically acceptable salt. Examples of the salt include, salts formed with inorganic base, salts formed with organic base, salts formed with inorganic acid, salts formed with organic acid, salts formed with basic or acidic amino acid and the like.

Preferable examples of the salt formed with inorganic base include alkali metal salts such as sodium salt, potassium salt and the like; alkaline earth metal salts such as calcium salt, magnesium salt and the like; and aluminum salt, ammonium salt and the like.

Preferable examples of the salt formed with organic base include salts formed with trimethylamine, triethylamine, pyridine, picoline, ethanolamine, diethanolamine, triethanolamine, dicyclohexylamine, N,N-dibenzylethylenediamine and the like.

Preferable examples of the salt formed with inorganic acid include salts formed with hydrochloric acid, hydrobromic acid, nitric acid, sulfuric acid, phosphoric acid and the like.

Preferable examples of the salt formed with organic acid include salts formed with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt formed with basic amino acid include salts formed with arginine, lysin, ornithine and the like, preferable examples of the salt formed with acidic amino acid include salts formed with aspartic acid, glutamic acid and the like.

Of the above-mentioned salts, sodium salt, potassium salt, hydrochloride and the like are preferable.

The reaction between compound (I) and compound (II) (hereinafter sometimes to be briefly referred to as reaction A) is carried out in an amide in the presence of a metal alkoxide.

As used herein, the metal alkoxide is, for example, alkali metal $C_{1-6}$ alkoxide. Examples thereof include tert-butoxide, methoxide, ethoxide and the like of sodium, potassium and lithium. The metal alkoxide is preferably alkali metal $C_{1-6}$ alkoxide, more preferably sodium tert-butoxide.

While the amount of a metal alkoxide to be used varies depending on the amide to be used and reaction temperature, it is generally 0.5–20 equivalents, preferably 2–20 equivalents, more preferably 2–5 equivalents, relative to compound (II). That is, the metal alkoxide is used in an amount of 50–2000 mol %, preferably 200–2000 mol %, more preferably 200–500 mol %, relative to compound (II).

As the amides, for example, N,N-dimethylformamide, acetamide, N,N-dimethylacetamide, 1-methyl-2-pyrrolidone, 1,3-dimethyl-2-imidazolidinone and the like are used. The amides preferably include N,N-dimethylformamide, N,N-dimethylacetamide, 1-methyl-2-pyrrolidone and 1,3-dimethyl-2-imidazolidinone, particularly preferably N,N-dimethylacetamide. Only one kind of these amides or two or more kinds thereof may be used at a suitable mixing ratio.

In the reaction of compound (I) with compound (II), the equivalent ratio of compound (I):compound (II) is about 5:1–about 1:5, preferably about 1:1–2. That is, compound (II) is used in an amount of about 20–about 500 mol %, preferably about 100–about 200 mol %, relative to compound (I).

The reaction of compound (I) with compound (IV) (hereinafter sometimes to be briefly referred to as reaction B) is carried out in an amide in the presence of a metal carbonate.

As used herein, the metal carbonate is exemplified by sodium, potassium, lithium, calcium, cecium, rubidium and the like. The metal carbonate is preferably alkali metal carbonate, more preferably potassium carbonate.

The metal carbonate is used in an amount of generally 20–500 mol %, preferably 50–200 mol %, relative to compound (IV).

The amides are exemplified by those recited as the amides for the aforementioned reaction A. Of those, N,N-dimethylformamide and the like are preferable.

In the reaction of compound (I) with compound (IV), the equivalent ratio of compound (I):compound (IV) is about 5:1–about 1:5, preferably about 1:1–2. That is, compound (IV) is used in an amount of about 20–about 500 mol %, preferably about 100–about 200 mol %, relative to compound (I).

The order of charging reaction A and reaction B is not particularly limited as long as it does not influence the reaction.

For example, (a) a metal alkoxide or metal carbonate may be added to a mixture of compound (I) with compound (II) or a mixture of compound (I) with compound (IV), respectively or (b) a mixture of compound (I) with compound (II) or a mixture of compound (I) with compound (IV), or each one of them may be added successively to metal alkoxide or metal carbonate, respectively, which is dissolved or suspended in advance in amides, or (c) compound (II) or compound (IV) is added to metal alkoxide or metal carbonate, respectively, which is dissolved or suspended in advance in amides to prepare a solution or suspension, and compound (I) dissolved or suspended in amides may be added thereto.

The reaction temperature of reaction A and reaction B varies depending on the kind of metal alkoxide, metal carbonate and the amides to be used. The temperature may be in the range of from −78° C. to the boiling point of amides, preferably from −5° C. to the boiling point of amides (e.g., 200° C.). The reaction temperature is more preferably −5° C. to 80° C.

The reaction time of reaction A and reaction B is, for example, 0.5–20 hours.

In the reaction A and reaction B, the reaction may be carried out in the presence of a quaternary ammonium salt, such as tetrabutylammonium bromide and the like; an alkali or alkali metal salt, such as potassium iodide, sodium iodide, potassium bromide, sodium bromide and the like; crown ether and the like, to promote the reaction.

The compound (III) obtained in reaction A may be amidated as noted below to produce compound (V).

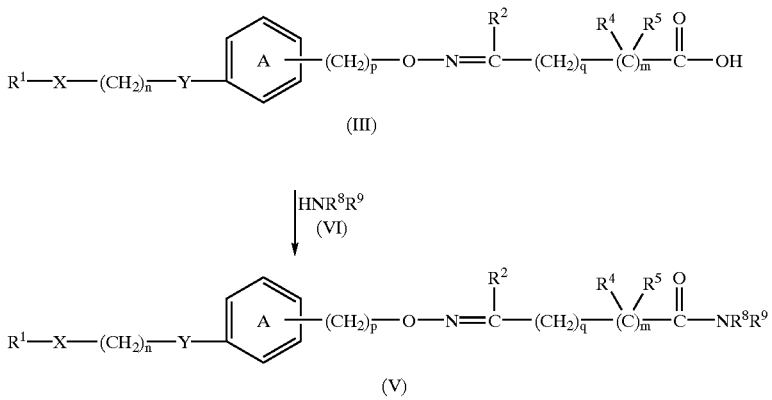

The amidation reaction is carried out according to a method known per se. That is, a method wherein compound (III) and a compound represented by the formula

wherein the symbols in the formula are as defined above, or a salt thereof (the salt is exemplified by those recited as the salt of compound (I) and the like) are directly condensed using a condensing agent (e.g., dicyclohexylcarbodiimide and the like), a method wherein a reactive derivative of compound (III) and compound (VI) are reacted appropriately, a method described in Organic Functional Group Preparations, Second Edition, pp. 316–355, ACADEMIC PRESS INC., or other method is used.

As used herein, the reactive derivative of compound (III) is exemplified by acid anhydride, acid halide (acid chloride, acid bromide), imidazolide, a mixed acid anhydride (e.g., anhydride with methyl carbonate, ethyl carbonate or isobutyl carbonate and the like) and the like. For example, when an acid halide is used, the reaction is carried out in the presence of a base in a solvent that does not influence the reaction. As the base, for example, triethylamine, N-methylmorpholine, N,N-dimethylaniline, sodium hydrogencarbonate, sodium carbonate, potassium carbonate and the like are mentioned. As the solvent that does not influence the reaction, for example, halogenated hydrocarbons such as chloroform, dichloromethane and the like; aromatic hydrocarbons such as benzene, toluene and the like; ethers such as tetrahydrofuran, dioxane and the like, ethyl acetate, water and the like are mentioned. These solvents may be mixed for use at a suitable mixing ratio. The amount of compound (VI) to be used is 1–10 molar equivalents, preferably 1–3 molar equivalents, relative to compound (III). The reaction temperature is generally from –30° C. to 100° C., and the reaction time is 0.5–20 hours. When a mixed acid anhydride is used, compound (III) and chlorocarbonate (e.g., methyl chlorocarbonate, ethyl chlorocarbonate, isobutyl chlorocarbonate and the like) are reacted in the presence of a base (e.g., triethylamine, N-methylmorpholine, N,N-dimethylaniline, sodium hydrogencarbonate, sodium carbonate, potassium carbonate and the like), and then the reaction mixture is reacted with compound (VI). The amount of compound (VI) to be used is 1–10 molar equivalents, preferably 1–3 molar equivalents, relative to compound (III). The reaction temperature is generally from –30° C. to 100° C., and the reaction time is 0.5–20 hours.

The compound (III) and compound (V) thus obtained can be separated and purified by a known separation and purification means, such as concentration, concentration under reduced pressure, solvent extraction, crystallization, recrystallization, phase transfer, treatment with activated carbon and the like. That is, the treatment after reaction may be extraction by a method known per se, such as extraction with a mixed solvent of an organic solvent insoluble or sparingly soluble in water and water. The organic solvent insoluble or sparingly soluble in water may be any as long as the objective compound can be dissolved, and is preferably aromatic hydrocarbons such as toluene; esters such as ethyl acetate and the like; ethers such as diisopropyl ether, t.-butyl methyl ether, tetrahydrofuran and the like.

Where necessary, employed is a washing process comprising maintaining the reaction mixture after completion of the reaction basic for dissolution of the objective compound in a salt form in water, washing the obtained solution with an organic solvent insoluble or sparingly soluble in water, and making the solution acidic to return the salt to the objective compound in a free form. Further employed is a washing process comprising washing an organic solvent insoluble or sparingly soluble in water, which contains the objective compound in a free form, with brine having an optional concentration or water.

In addition, the objective compound may be purified by a method known per se, such as recrystallization and the like. The recrystallization may be conducted utilizing the difference in solubility under heating conditions and in a solvent (e.g., diisopropyl ether, t.-butyl methyl ether, n-hexane and the like) in which the objective compound is insoluble or sparingly soluble at a particular temperature, or utilizing the difference in solubility of a mixed solvent, by dissolving the objective compound in a solvent (e.g., tetrahydrofuran, acetone and the like) in which the compound is soluble or easily soluble, and adding a solvent (e.g., diisopropyl ether, t.-butyl methyl ether, n-hexane, water and the like) in which the objective compound is insoluble or sparingly soluble, and the like.

The starting material compound used for each of the aforementioned reactions can be synthesized by, for example, the following method.

The compound (I) can be synthesized by, (1) reacting butanedione oxime with benzaldehyde in the presence of an acid to convert the compound to N-oxide, reacting this compound with xalyl chloride, phosphorus oxychloride and the like to give a chloromethyl compound, according to the method described in Chemical and Pharmaceutical Bulletin, vol. 19, p. 2050 (1970), (2) converting the chloromethyl compound to a benzaldehyde compound by reacting the chloromethyl compound with p-hydroxybenzyl alcohol in the presence of a base according to the method described in Journal of Chemical Society, Chemical Communications, vol. 9, p. 582 (1988), or reacting the chloromethyl compound with p-hydroxybenzaldehyde in the presence of a base according to the method described in Journal of Organic Chemistry, vol. 57, p. 589 (1992), reducing this compound with a reducing agent, such as sodium borohydride and the like, according to the method described in Tetrahedron Letters, vol. 28, p. 2473 (1987), to synthesize a hydroxymethyl compound, and (3) reacting this compound with thionyl chloride and the like, according to the method described in Journal of Medicinal Chemistry, vol. 29, p. 1589 (1986). The compound (I) can be also synthesized according to a method similar to these methods.

The compound (II) and compound (IV) can be synthesized according to the method described in Pharmazie, vol. 38, p. 313 (1983) or Acta Crystallographica, vol. C50, p. 78 (1994), namely, according to a method comprising reacting ketone and hydroxyamine in the presence of a base, or a method similar to these methods.

The compound (I), compound (II) and compound (IV) thus obtained may be respectively used for the production method of the present invention after separation and purification by a known means, or used as a reaction mixture for the production method of the present invention.

BEST MODE FOR EMBODIMENT OF THE INVENTION

The present invention is explained in the following by referring to Reference Examples and Examples, which are not to be construed as limitative.

EXAMPLES

Reference Example 1

Production of 4-(hydroxyimino)-4-phenylbutanoic acid

Benzoylpropionic acid (100 g) was suspended in methanol (300 ml) at room temperature, and hydroxyamine hydrochloride (46.8 g) and sodium acetate (138 g) were added. After stirring the mixture for 4.5 hr at room temperature at 22–27° C., pure water (500 ml) was added under cooling at 24–26° C. Seed crystal was added at 25° C., and the mixture was stirred at room temperature for about 1 hr, then cooled to 10° C. over about 30 min, and stirred at 5–10° C. for about 2 hr. The precipitated solid was collected by filtration, washed with pure water (100 ml×2) and dried under reduced pressure (40° C.) to give 4-(hydroxyimino)-4-phenylbutanoic acid (94.4 g) as a white solid in a yield of 87.1%.

$^1$H-nuclear magnetic resonance spectrum (DMSO-$d_6$-300 MHz) δ ppm 2.40(2H,t,7.6 Hz), 2.71(2H,t,7.6 Hz), 7.37–7.42(3H,m), 7.62–7.65(2H,m), 11.31(1H,s), 12.15(1H, s)

Reference Example 2

Step 1: Production of 4-(chloromethyl)-5-methyl-2-phenyl-1,3-oxazole

Benzaldehyde (342 g) and acetic acid (800 ml) were added to 2,3-butanedione oxime (300 g), and the mixture was stirred for dissolution at room temperature, followed by cooling. Hydrochloric acid gas was started to be blown into the mixture at 5° C., and hydrochloric acid gas was continuously blown at 10–25° C. for 5 hr. Diisopropyl ether (1200 ml) was added at 10–15° C. over about 1 hr, and the mixture was aged at 5–10° C. for 1 hr. The precipitated solid was collected by filtration and washed twice with diisopropyl ether (400 ml) to give a pale-yellow white solid (not dried, 527 g) . 120 g therefrom was suspended in tetrahydrofuran (360 ml), cooled, and a solution of thionyl chloride (117 ml, 191 g) in tetrahydrofuran (240 ml) was added at 3–6° C. over about 40 min. The mixture was heated to 25° C. over about 1 hr, stirred with heating under reflux (66° C.) for 6 hr. The mixture was cooled to 27° C. over about 1 hr, and stirred under ice-cooing at 5–10° C. for 1 hr. The precipitated solid was collected by filtration and washed with tetrahydrofuran (24 ml×2) to give 4-(chloromethyl)-5-methyl-2-phenyl-1,3-oxazole (not dried, 119 g) as a pale-yellow white solid. Acetonitrile (57.9 ml) was added (suspended) to 23.7 g therefrom and pure water (9.7 ml) was added for dissolution at 21° C. Pure water (96.5 ml) was added at 21–24° C. over about 1 hr, and the mixture was cooled and stirred at 5–10° C. for 3 hr. The precipitated solid was collected by filtration, washed with pure water (20 ml×2) and dried under reduced pressure (40° C.) to give 4-(chloromethyl)-5-methyl-2-phenyl-1,3-oxazole (15.9 g) as a pale-yellow white solid in a yield of 56.7%.

$^1$H-nuclear magnetic resonance spectrum (CDCl$_3$-300 MHz) δ ppm 4.73(3H,s), 4.46(2H,s), 7.41–7.46(3H,m), 7.99–8.02(2H,m)

Step 2: Production of {4-[(5-methyl-2-phenyl-1,3-oxazol-4-yl)methoxy]phenyl}methanol 4-(Chloromethyl)-5-methyl-2-phenyl-1,3-oxazole (50.0 g) was dissolved in dimethyl acetamide (200 ml) and parahydroxybenzaldehyde (30.9 g) and potassium carbonate (49.9 g) were added at room temperature. The mixture was heated and stirred at 50–65° C. for 4 hr. The mixture was cooled, and sodium borohydride (9.11 g) was added at 5–13° C. After stirring for about 5 min, the mixture was stirred at room temperature for 4 hr. Under ice-cooling, methanol (50 ml) was added at 20–21° C., and water (50 ml) was added at 21–24° C. under ice-cooling. Under ice-cooling, conc. hydrochloric acid (50 ml) was added at 18–25° C. and water (50 ml) was added under ice-cooling at 23° C. Stirring was stopped and the reaction mixture was stood overnight at room temperature. The precipitated solid was collected by filtration and washed twice with water (150 ml). The solid was dried under reduced pressure (40° C.) to give {4-[(5-methyl-2-phenyl-1,3-oxazol-4-yl)methoxy] phenyl}methanol (68.3 g) as a pale-yellow brown solid in a yield of 96.0%.

$^1$H-nuclear magnetic resonance spectrum (CDCl$_3$-300 MHz) δ ppm 2.44(3H,s), 4.62(2H,s), 5.00(2H,s), 5.16(2H,s), 7.01(2H,d,J=7 Hz), 7.31(2H,d,J=7 Hz), 7.42–7.46(3H,m), 8.00–8.03(2H,m)

Step 2': Production of {4-[(5-methyl-2-phenyl-1,3-oxazol-4-yl)methoxy]phenyl}methanol 4-(Chloromethyl)-5-methyl-2-phenyl-1,3-oxazole (5.00 g), parahydroxybenzyl alcohol (3.29 g) and potassium carbonate (6.66 g) were suspended in dimethylformamide (25 ml) and the suspension was stirred at 50° C. for 3.5 hr. The reaction mixture was cooled and water (25 ml) was added at not higher than 15° C. The mixture was stirred for about 5 min and at about 5° C. for 1 hr under ice-cooling. The crystals were collected by filtration, washed twice with water (15 ml) and dried under reduced pressure at 50° C. to give the objective product (6.85 g) in a yield of 96%.

$^1$H-nuclear magnetic resonance spectrum (CDCl$_3$-300 MHz) δ ppm 2.44(3H,s), 4.62(2H,s), 5.00(2H,s), 5.16(2H,s), 7.01(2H,d,J=7 Hz), 7.31(2H,d,J=7 Hz), 7.42–7.46(3H,m), 8.00–8.03(2H,m)

Step 3: Production of 4-{[4-(chloromethyl)phenoxy]methyl}-5-methyl-2-phenyl-1,3-oxazole {4-[(5-Methyl-2-phenyl-1,3-oxazol-4-yl)methoxy]phenyl}-methanol (300 g), tetrahydrofuran (750 ml) and toluene (750 ml) were charged and the mixture was cooled to 5° C. Thionyl chloride (88 ml) was added dropwise at not higher than 15° C. over 10 min and the mixture was reacted at 10–15° C. for 1 hr. 10% Brine (900 ml) was added dropwise at the same temperature over about 10 min, and the mixture was stood for 30 min, partitioned and activated carbon (15 g) was added to the organic layer. The mixture was stirred for about 1 hr, and the activated carbon was filtered off and the mixture was washed with toluene (300 ml). The organic layer was concentrated to about 805 g and then heated to about 60° C. to dissolve crystals, followed by standing for cooling. The mixture was cooled to about 25° C. over 30 min and n-hexane (1800 ml) was added dropwise over about 30 min. The mixture was cooled to around 5° C. and aged for 1 hr. The crystals were collected by filtration and washed with cold toluene-n-hexane (1:3) (600 ml). The crystals were dried under reduced pressure at 40° C. to give pale-yellow 4-{[4-(chloromethyl)phenoxy]methyl}-5-methyl-2-phenyl-1,3-oxazole (280.0 g) in a yield of 87.9%.

$^1$H-nuclear magnetic resonance spectrum (CDCl$_3$-300 MHz) δ ppm 2.43(3H,s), 4.57(2H,s), 5.00(2H,s), 7.01(2H,d,J=7 Hz), 7.32(2H,d,J=7 Hz), 7.41–7.46(3H,m), 8.00–8.03(2H,m)

Reference Example 3

Production of 8-(hydroxyimino)-8-phenyloctanoic acid

Ethyl benzoylacetate (2.50 g), ethyl 6-bromohexanate (3.67 g), potassium carbonate (2.25 g) and sodium iodide (2.50 g) were suspended in 1-methyl-2-piperidone (12.5 ml) and the suspension was stirred at 60° C. for 6 h. To the reaction mixture were added water (25 ml) and toluene (7.5 ml), and the mixture was extracted. The toluene layer was washed with water (7.5 ml) and concentrated under reduced pressure to give a yellow oil. The concentrate was dissolved in methanol (7.5 ml) and concentrated again. The yellow oil was dissolved in ethanol denatured by methanol (12.5 ml) and 4N sodium hydroxide solution (12.5 ml) was added at room temperature. The mixture was refluxed for 1 hr and cooled to not higher than room temperature (25° C.). Hydroxyamine hydrochloride (1.08 g) was added and the mixture was refluxed for 9 hr. The mixture was allowed to cool to room temperature (not higher than 25° C.) and 3N hydrochloric acid (9 ml) was added dropwise, which was followed by crystallization. The crystals were aged under ice-cooling for 1 hr, collected by filtration and washed with water (10 ml). The crystals were dried in vacuo at 40° C. for 3 hr to give pale-yellow crystals. The obtained crystals were suspended in acetone (12.5 ml) and distilled water (12.5 ml), and dissolved under reflux. The mixture was allowed to cool to room temperature, crystallized and aged under ice-cooling for 1 hr. The obtained crystals were filtrated, washed with distilled water (12.5 ml) and dried in vacuo at 40° C. for 4 hr to give the objective product as pale-yellow crystals (1.96 g, yield 60.4%).

$^1$H-nuclear magnetic resonance spectrum (DMSO-d$_6$-300 MHz) δ ppm;1.28–1.50(8H,m), 2.17(2H,t,J=7), 2.71(2H,t, J=7 Hz), 7.37–7.45(3H,m), 7.61–7.67(2H,m), 11.10(1H,s), 12.01(1H,br)

Reference Example 4

Production of 4-[({4-[(5-methyl-2-phenyl-1-3-oxazol-4-yl)methoxy]benzyl}oxy)imino]-4-phenylbutylamide (E)-4-[({4-[(5-Methyl-2-phenyl-1-3-oxazol-4-yl)methoxy]benzyl}oxy)imino]-4-phenylbutanoic acid (0.5 g) was dissolved in ethyl acetate (5 ml) and ice-cooled. Triethylamine (0.18 ml) was stirred at the same temperature for 10 min and ethyl chloroformate (0.14 g) was added dropwise on continuous ice-cooling. The mixture was stirred for 30 min with ice-cooling. Under ice-cooling, conc. aqueous ammonia (0.5 ml) was added dropwise and the mixture was stirred at the same temperature for 30 min. The reaction mixture was allowed to return to room temperature, and after stirring for 1 hr, diisopropyl alcohol (5 ml) was added. The mixture was stirred under ice-cooling for 1 hr and filtrated. The obtained crystals were washed with cold diisopropyl alcohol (3 ml) and dried in vacuo at 50° C. for 3 hr to give the objective product as white crystals (0.43 g, 0.92 mmol, yield 86.4%).

$^1$H-nuclear magnetic resonance spectrum (CDCl$_3$-300 MHz) δ ppm;2.41–2.49(5H,m), 3.04–3.10(2H,t,J=7 Hz), 5.05(3H,s), 5.18(2H,s), 5.18(1H,br), 5.45(1H,br), 7.00(2H, d,J=7 Hz), 7.35–7.38(5H,m), 7.42–7.45(3H,m), 7.63–7.66 (2H,m), 8.00–8.03(2H,m)

Reference Example 5

Production of 4-(hydroxyimino)-4-phenylbutylamide

4-Oxo-4-phenylbutylamide (60.0 g) was suspended in methanol (216 ml) and hydroxyamine hydrochloride (25.8 g) and sodium acetate (30.6 g) were added at room temperature. The mixture was stirred at 25° C. for 2 hr. Pure water (360 ml) was added at 25–26° C. and seed crystal (0.5 mg) was added at 22° C. After stirring at room temperature for 30 min, the mixture was cooled to 10° C. over about 1 hr and stirred at 5–10° C. for 1 hr. The precipitated solid was collected by filtration, washed with pure water (50 ml) and dried under reduced pressure (40° C.) to give 4-(hydroxyimino)-4-phenylbutylamide (34.5 g) as a pale-purple white solid in a yield of 53.0%.

$^1$H-nuclear magnetic resonance spectrum (DMSO-d$_6$-300 MHz) δ ppm; 2.19–2.27(2H, m), 2.86–2.92(2H, m), 6.80 (1H, brs), 7.31(1H, brs), 7.35–7.42(3H, m), 7.63–7.66(2H, m), 11.25(1H, s).

Reference Example 6

Production of {4-[(5-methyl-2-phenyl-1,3-oxazol-4-yl)methoxy]phenyl}methanol (1) 2,3-Butanedione oxime (300 g) and benzaldehyde (342 g) were added to acetic acid (900 ml) and the mixture was stirred. Hydrochloric acid gas (311 g) was blown into the obtained solution at 10–25° C. and diisopropyl ether (1200 ml) was added under cooling. The reaction mixture was stirred at 0–10° C. for 1 hr. The precipitated solid was collected by filtration, washed twice with diisopropyl ether (400 ml), and dried in vacuo at 25° C. to give a pale-yellow white solid (524.5 g). This solid (21.72 g) was suspended in a mixed solvent of toluene (130 ml) and N,N-dimethylformamide (2.4 ml). The obtained suspension was heated to 70–75° C., and thionyl chloride (8.84 ml) was added and the mixture was stirred for 1.5 hr. The reaction mixture was cooled to 25–30° C. and water (132 ml) was added. The mixture was stirred and stood still. The organic layer was separated and washed with 7% aqueous sodium hydrogencarbonate solution (132 ml). N,N-Dimethylacetamide (40 ml) was added and the mixture was concentrated under reduced pressure.

(2) Separately, under a nitrogen gas stream, parahydroxybenzyl alcohol (11.92 g) was dissolved in N,N-dimethylacetamide (40 ml) and 28% sodium methoxide (20.4 g) was added dropwise at not higher than 15° C. The obtained mixture was heated to 25° C. and the mixture was stirred for 1 hr. The obtained solution was added dropwise to the concentrate obtained in the aforementioned (1) at 25° C. over 0.5 hr and the mixture was stirred at 50° C. for 3 hr. Water (20 ml) was added to the reaction mixture and 2N hydrochloric acid (6 ml) was added dropwise at 25° C. to adjust the mixture to pH 7. Methanol (18 ml) and toluene (120 ml) were added to the obtained mixture and water (200 ml) was added dropwise. The mixture was stirred for 0.5 hr and the obtained mixture was cooled to 0–10° C. and stirred for 1 hr. The precipitated crystals were collected by filtration and washed twice with water (100 ml). The obtained wet crystals were dissolved by heating in tetrahydrofuran (112 ml) at 30–40° C., and after stirring for 15 min, the mixture was gradually cooled to 25° C. To the obtained solution was added dropwise water (170 ml) at the same temperature, and after stirring for 1 hr, the mixture was cooled and stirred for 1 hr. The precipitated crystals were collected by filtration, washed with water (40 ml), and dried under reduced pressure to give the objective product (19.4 g, yield 53.4%).

$^1$H-nuclear magnetic resonance spectrum (CDCl$_3$-300 MHz) δ ppm 2.44(3H,s), 4.62(2H,s), 5.00(2H,s), 5.16(2H,s), 7.01(2H,d,J=7 Hz), 7.31(2H,d,J=7 Hz), 7.42–7.46(3H,m), 8.00–8.03(2H,m)

Example 1

Production of (E)-4-[({4-[(5-methyl-2-phenyl-1-3-oxazol-4-yl)methoxy]benzyl}oxy)imino]-4-phenylbutanoic acid Sodium tert.-butoxide (3.22 g) and dimethylacetamide (35 ml) were charged and dissolved with stirring. The mixture was cooled to around 15° C. and a solution of 4-(hydroxyimino)-4-phenylbutanoic acid (3.30 g) in dimethylacetamide (5 ml) was added dropwise at 14–17° C. over 10 min, and the mixture was aged with stirring at around 15° C. for 1 hr. 4-{[4-(Chloromethyl)phenoxy]methyl}-5-methyl-2-phenyl-1,3-oxazole (5.0 g) was divided into four portions and each portion was added thereto every 10 min at 15–16° C. The mixture was then reacted at room temperature for about 5.5 hr. To the reaction mixture were added water (25 ml) and 1N-NaOH (1 ml) in this order and the mixture was stirred at around 20° C. for 1 hr. Toluene (10 ml) was added and the mixture was stirred. After partitioning, the aqueous layer (77.3 g) was concentrated until the weight of the content became 59.4 g. To this aqueous layer was added dropwise 2N-HCl at around 25° C. to adjust the mixture to pH 7.0. Seed crystal was added and the mixture was stirred for 1 hr to allow precipitation of crystals. 2N-HCl was further added dropwise over 15 min to adjust the mixture to pH 4.0. The mixture was stirred for 1 hr to age the crystals. The crystals were filtered, washed with water and dried under reduced pressure at 40° C. to give 4-[({4-[(5-methyl-2-phenyl-1-3-oxazol-4-yl)methoxy]benzyl}oxy)imino]-4-phenylbutanoic acid (6.56 g) as white crystals in a yield of 87.5%. The crystals were dissolved in acetone (38 ml) with heating under reflux and a suspension (2 ml) of activated carbon (0.33 g) in acetone was added. After stirring with heating under reflux for 10 min, activated carbon was filtered off and washed with heated acetone (16 ml). The mother liquor and washing solution were combined and gradually cooled by stirring. The mixture was stirred at 35–40° C. for 3 hr and cooled to around 25° C. over 30 min, and stirred at the same temperature for 3 hr. The mixture was left standing at room temperature overnight and cooled to 5° C. in 30 min. The mixture was stirred at the same temperature for 3 hr. Purified water (40 ml) was added at around 5° C. over 30 min and the mixture was stirred at the same temperature for 3 hr. The precipitated crystals were collected by filtration and washed twice with purified water (30 ml). The crystals were dried under reduced pressure at 50° C. to give (E)-4-[({4-[(5-methyl-2-phenyl-1-3-oxazol-4-yl)methoxy]benzyl}oxy)imino]-4-phenylbutanoic acid (5.8 g) as white crystals in a yield of 89%.

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 2

Production of (E)-4-[({4-[(5-methyl-2-phenyl-1-3-oxazol-4-yl)methoxy]benzyl}oxy)imino]-4-phenylbutanoic acid (method without isolation of 4-{[4-(chloromethyl)phenoxy]-methyl}-5-methyl-2-phenyl-1,3-oxazole in Reference Example 2, step 3)

(4-[(5-Methyl-2-phenyl-1,3-oxazol-4-yl)methoxy]-phenyl}methanol (5.0 g), tetrahydrofuran (12.5 ml) and toluene (12.5 ml) were charged and cooled to 2.5° C. Thionyl chloride (1.5 ml) was added dropwise at 2.5–15° C. and the mixture was reacted at 12–15° C. for 1 hr. 10% Brine (15 ml) was added dropwise at 12–15° C., and after stirring, the mixture was partitioned. The organic layer was concentrated to about 15 g, and N,N'-dimethylacetamide (10 ml) was added to the concentrate to dissolve the crystals. The mixture was further concentrated under reduced pressure and toluene was distilled to give a reaction mixture (about 15 g). To the reaction mixture were added 4-(hydroxyimino)-4-phenylbutanoic acid (3.50 g) and N,N'-dimethylacetamide (15 ml) and dissolved therein, after which nitrogen was introduced into the reactor. After cooling to 5° C., a solution of sodium tert.-butoxide (3.41 g) in N,N'-dimethylacetamide (10 ml) was added dropwise at 3–8° C. over about 10 min. After stirring at around 5° C. for 30 min, the mixture was heated to 25° C. over 15 min, and reacted at around 25° C. for about 5 hr with stirring. 1N-NaOH (1 ml) was added and the mixture was stirred at around 30° C. for 1 hr. Toluene (10 ml) and water (19 ml) were added, and after stirring the mixture for 5 min, the aqueous layer (65.0 g) was separated and concentrated to 49 g. To this aqueous layer maintained near 25° C. was added dropwise 2N-HCl to adjust the mixture to pH 7.0. Seed crystal was added and the mixture was stirred for 1 hr to allow precipitation of crystals. 2N-HCl was further added dropwise over 15 min to adjust the mixture to pH 4.0. The mixture was stirred for 1 hr to age the crystals. The crystals were collected by filtration, washed with water and dried under reduced pressure at 50° C. to give the objective compound as yellow-white crystals (6.11 g, yield 77%).

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 3

Purification of (E)-4-[({4-[(5-methyl-2-phenyl-1-3-oxazol-4-yl)methoxy]benzyl}oxy)imino]-4-phenylbutanoic acid (using tetrahydrofuran and tert-butyl methyl ether)

(E)-4-[({4-[(5-Methyl-2-phenyl-1-3-oxazol-4-yl)methoxy]benzyl}oxy)imino]-4-phenylbutanoic acid (4.00 g) was dissolved in tetrahydrofuran (12 ml) (at 27° C.). tert-Butyl methyl ether (16 ml) was added at room temperature (25–27° C.) and the mixture was stirred for 1 hr. tert-Butyl methyl ether (12 ml) was further added at the same temperature and the mixture was stirred for 1.5 hr. The mixture was ice-cooled and after stirring at around 5° C. for 3 hr, the precipitated solid was collected by filtration, washed twice with tert-butyl methyl ether (4 ml) and dried under reduced pressure (50° C.) to give (E)-4-[({4-[(5-methyl-2-phenyl-1-3-oxazol-4-yl)methoxy]benzyl}oxy)imino]-4-phenylbutanoic acid (3.27 g) as a white solid in a yield of 81.8%.

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 4

Purification of (E)-4-[({4-[(5-methyl-2-phenyl-1-3-oxazol-4-yl)methoxy]benzyl}oxy)imino]-4-phenylbutanoic acid (using tetrahydrofuran and n-hexane)

(E)-4-[({4-[(5-Methyl-2-phenyl-1-3-oxazol-4-yl)methoxy]benzyl}oxy)imino]-4-phenylbutanoic acid (1.38 g) was dissolved in tetrahydrofuran (4.2 ml) (near 25° C.). n-Hexane (4.2 ml) was added at room temperature (25° C.) and the mixture was stirred for about 10 min. The mixture was ice-cooled, and after stirring at near 5° C. for 30 min, the precipitated solid was collected by filtration and dried under reduced pressure (40° C.) to give (E)-4-[({4-[(5-methyl-2-phenyl-1-3-oxazol-4-yl)methoxy]benzyl}oxy)imino]-4-phenylbutanoic acid (0.93 g) as a white solid in a yield of 67.4%.

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 5

Purification of (E)-4-[({4-[(5-methyl-2-phenyl-1-3-oxazol-4-yl)methoxy]benzyl}oxy)imino]-4-phenylbutanoic acid (using tetrahydrofuran and diisopropyl ether)

(E)-4-[({4-[(5-Methyl-2-phenyl-1-3-oxazol-4-yl)methoxy]benzyl}oxy)imino]-4-phenylbutanoic acid (5.00 g) was 10 dissolved in tetrahydrofuran (15 ml) (at 26° C.). Diisopropyl ether (20 ml) was added at room temperature (25–27° C.) and the mixture was stirred for 1 hr. The mixture was ice-cooled, and after stirring at near 5° C. for 2 hr, the precipitated solid was collected by filtration, washed twice with diisopropyl ether (5 ml), and dried under reduced pressure (50° C.) to give (E)-4-[({4-[(5-methyl-2-phenyl-1-3-oxazol-4-yl)methoxy]benzyl}oxy)imino]-4-phenylbutanoic acid (4.02 g) as a white solid in a yield of 80.4%.

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 6

Purification of (E)-4-[({4-[(5-methyl-2-phenyl-1-3-oxazol-4-yl)methoxy]benzyl}oxy)imino]-4-phenylbutanoic acid (using acetone, tetrahydrofuran and water)

(E)-4-[({4-[(5-Methyl-2-phenyl-1-3-oxazol-4-yl)methoxy]benzyl}oxy)imino]-4-phenylbutanoic acid (4.00 g) was suspended in acetone (16 ml) (at 25° C.). Tetrahydrofuran (12 ml) was added at room temperature (25° C.) for dissolution. The mixture was ice-cooled, and after stirring at around 5° C. for 8.5 hr, the reaction mixture was stood overnight in a refrigerator. The reaction mixture was ice-cooled and H$_2$O (12 ml) was added at around 5° C., and the mixture was stirred at the same temperature at around 5° C. for 8.5 hr. The precipitated solid was collected by filtration, washed twice with water (4 ml), and dried (40° C.) under reduced pressure to give (E)-4-[({4-[(5-methyl-2-phenyl-1-3-oxazol-4-yl)methoxy]benzyl}oxy)imino]-4-phenylbutanoic acid (3.22 g) as a white solid in a yield of 80.5%.

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 7

Production of (E)-8-[({4-[(5-methyl-2-phenyl-1,3-oxazol-4-yl)methoxy]benzyl}oxy)imino]-8-phenyloctanoic acid (E)-8-(Hydroxyimino)-8-phenyloctanoic acid (1.0 g) and 4-{[4-(chloromethyl)phenoxy]methyl}-5-methyl-2-phenyl-1,3-oxazole (1.26 g) were dissolved in 1-methyl-2-pyrrolidone (10 ml), and the solution was ice-cooled. Sodium tert-butoxide (0.85 g) was added to the reaction mixture at not higher than −5° C. and the mixture was stirred at the same temperature for 30 min, and then at room temperature for 4 hr. 1N Hydrochloric acid was added to the reaction mixture and the mixture was extracted with ethyl acetate (20 ml). The organic layer was washed with 10% brine (20 ml) and dried over anhydrous sodium sulfate. The organic layer was concentrated and acetone/water (1/1) (20 ml) was added to the obtained residue (brown oil). The mixture was dissolved under reflux and allowed to cool for crystallization. The crystals were collected by filtration, washed with H$_2$O (5 ml) and dried in vacuo at 50° C. for 4 hr. Acetone/water (2/1) (30 ml) was added to the obtained crystals, the mixture was dissolved under reflux, and allowed to cool for crystallization. The crystals were collected by filtration and washed with water (5 ml). The crystals were dried in vacuo at 0° C. for 4 hr, and the objective product was obtained as white crystals (1.55 g, yield 86%).

$^1$H-nuclear magnetic resonance spectrum (CDCl$_3$-300 MHz) δ ppm 1.14–1.17(4H,br), 1.30–1.46(4H,br), 2.09(2H, t,J=7 Hz), 2.46(3H,s), 2.74(2H,t,J=7 Hz), 5.00(2H,s), 5.16 (2H,s), 6.99(2H,d,J=7 Hz), 7.35–7.46(8H,m), 7.62–7.65 (2H,m), 8.00–8.03(2H,m)

Example 8

Production of (E)-4-[({4-[(5-methyl-2-phenyl-1-3-oxazol-4-yl)methoxy]benzyl}oxy)imino]-4-phenylbutylamide 4-{[4-(Chloromethyl)phenoxy]methyl}-5-methyl-2-phenyl-1,3-oxazole (1.00 g) was dissolved in N,N-dimethylformamide (3.0 ml), and 4-(hydroxyimino)-4-phenylbutylamide (613 mg) and anhydrous potassium carbonate (970 mg) were added at room temperature. The mixture was stirred at 50° C. for 4 hr. Acetone (4.0 ml) was added at the same temperature and pure water (5.0 ml) was added at the same temperature over about 20 min. The mixture was cooled to 30° C. over about 20 min and stirred at around 25° C. for about 1 hr. The precipitated solid was collected by filtration, washed twice with pure water (2 ml) and dried under reduced pressure (40° C.) to give (E)-4-[({4-[(5-methyl-2-phenyl-1-3-oxazol-4-yl)methoxy]benzyl) oxy}imino]-4-phenylbutylamide (1.20 g) as a pale-green white solid in a yield of 80.2%.

$^1$H-nuclear magnetic resonance spectrum (CDCl$_3$-300 MHz) δ ppm;2.41–2.49(5H,m), 3.04–3.10(2H,t,J=7 Hz), 5.05(3H,s), 5.18(2H,s), 5.18(1H,br), 5.45(1H,br), 7.00(2H, d,J=7 Hz), 7.35–38(5H,m), 7.42–7.45(3H,m), 7.63–7.66 (2H,m), 8.00–8.03(2H,m)

Example 9

Production of (E)-4-[({4-[(5-methyl-2-phenyl-1,3-oxazol-4-yl)methoxy]benzyl}oxy)imino]-4-phenylbutanoic acid (1) A mixture of {4-[(5-methyl-2-phenyl-1,3-oxazol-4-yl) methoxy]phenyl}methanol (5.0 g), tetrahydrofuran (12.5 ml) and toluene (12.5 ml) was cooled to not higher than 10° C. Thionyl chloride (1.44 ml) was added dropwise at not higher than 15° C., and the mixture was stirred at 20–30° C. for 1 hr. 10% Brine (25 ml) was added dropwise to the reaction mixture at 20–30° C. and left standing, and the organic layer was separated. To the organic layer was added 10% brine (25 ml) and the mixture was left standing, and the aqueous layer was separated. N,N-Dimethylacetamide (20 ml) was added to the organic layer, and the solvent (20–30 ml) was evaporated under reduced pressure at an outside temperature of 50–55° C. To the residue was added toluene (13 ml) and the solvent (8–18 ml) was evaporated under reduced pressure at an outside temperature of 50–55° C. To the residue was added toluene (13 ml) and the solvent (8–18 ml) was evaporated under reduced pressure at an outside temperature of 50–55° C.

(2) Separately, sodium tert-butoxide (2.92 g) was added to N,N-dimethylacetamide (25 ml) at 20–30° C. The obtained mixture was cooled to 15–20° C. and a solution of 4-(hydroxyimino)-4-phenylbutanoic acid (3.11 g) in dimethylacetamide (5 ml) was added dropwise and the mixture was stirred at 20–30° C. for 1 hr.

To the obtained solution was added dropwise at 20–30° C. the concentrate obtained in the aforementioned (1), and the mixture was stirred at the same temperature for 2 hr. To the resulting solution was added sodium tert-butoxide (0.33 g) at 20–30° C. and the mixture was stirred at the same temperature for 2 hr. The reaction mixture was cooled to not higher than 10° C., water (25 ml) was added dropwise, then 1N aqueous sodium hydroxide solution (1 ml) was added, and the mixture was stirred at 20–30° C. for 1 hr. To the mixture was added toluene (20 ml) and the mixture was stirred and left standing and the aqueous layer was separated. To the aqueous layer was added toluene (10 ml) and the mixture was stirred and left standing. The aqueous layer was separated and concentrated under reduced pressure. Thereto was added dropwise 2N hydrochloric acid at 20–30° C. to adjust the mixture to pH 7.0. The obtained mixture was stirred at 20–30°0 C. for 1 hr and 2N hydrochloric acid was added dropwise to adjust the mixture to pH 4. The obtained mixture was stirred at 20–30° C. for 1 hr and the precipitated crystals were collected by filtration. The obtained crystals were washed with water (20 ml) and dried in vacuo to give the objective product (6.19 g, yield 77.7%) as pale-yellow crystals.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Example 10

Purification of (E)-4-[({4-[(5-methyl-2-phenyl-1,3-oxazol-4-yl)methoxy]benzyl}oxy)imino]-4-phenylbutanoic acid (E)-4-[({4-[(5-Methyl-2-phenyl-1,3-oxazol-4-yl) methoxy]benzyl}oxy)imino]-4-phenylbutanoic acid (5.0 g) was dissolved in a mixed solvent of acetone (15 ml) and tetrahydrofuran (12.5 ml) at 32–34° C. To the obtained solution was added activated carbon (0.25 g) and the mixture was stirred at the same temperature for 0.5 hr and filtrated. The activated carbon was filtered off and washed with tetrahydrofuran (2.5 ml) and acetone (2.5 ml), and the washing solution was combined with the filtrate. To the obtained mixture was added water (17.5 ml) at 20–30° C. and the mixture was stirred at the same temperature for 1 hr and then at 35–40° C. for one more hour. The obtained mixture was gradually cooled to 20–30° C. and stirred at 0–10° C. for 1 hr, and the precipitated crystals were collected by filtration. The obtained crystals were washed with acetone/water=3/7 (10 ml) cooled to 0–10° C. and dried in vacuo to give the objective product (4.10 g, yield 82.0%) as a white solid.

melting point: 137–138° C.

$^1$H-nuclear magnetic resonance spectrum (CDCl$_3$-300 MHz) δ ppm 2.43(2H,s), 2.58(2H,t,7 Hz), 3.05(2H,t,7 Hz), 5.00(2H,s), 5.16(2H,s), 7.01(2H,m), 7.33–7.36(5H,m), 7.42–7.44(3H,m), 7.60–7.64(2H,m), 7.99–8.02(2H,m)

Industrial Applicability

According to the production method of the present invention, oxyimino-alkanoic acid derivatives (III) and (V) having an anti-diabetic activity can be obtained in a high yield and high quality without a purification step using silica gel column chromatography. In addition, the production method of the present invention is superior in operability. Therefore, the production method of the present invention is effective as an industrial production method.

What is claimed is:

1. A production method of a compound represented by the formula (III)

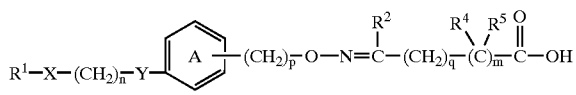

wherein

R$^1$ is an optionally substituted hydrocarbon group or an optionally substituted heterocyclic group;

X is a bond, —CO—, —CH(OH)— or —NR$^6$—(R$^6$ is a hydrogen atom or an optionally substituted alkyl group);

n is an integer of 1 to 3;

Y is an oxygen atom, a sulfur atom, —SO—, —SO$_2$— or —NR$^7$—(R$^7$ is a hydrogen atom or an optionally substituted alkyl group);

ring A is a benzene ring optionally having 1 to 3 additional substituents;

p is an integer of 1 to 8;

R$^2$ is a hydrogen atom or an optionally substituted hydrocarbon group or an optionally substituted heterocyclic group;

q is an integer of 0 to 6;

m is 0 or 1; and

R$^4$ and R$^5$ are the same or different and each is a hydrogen atom or an optionally substituted hydrocarbon group or R$^4$ may be bonded to R$^2$ to form a ring, or a salt thereof, which comprises reacting a compound represented by the formula (I)

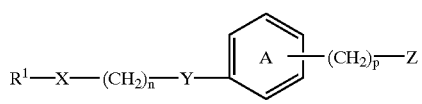

wherein Z is a halogen atom or OSO$_2$R$^{10}$ (R$^{10}$ is an alkyl group having 1 to 4 carbon atoms or an aryl group having 6 to 10 carbon atoms which is optionally substituted by alkyl group having 1 to 4 carbon atoms), and other symbols in the formula are as defined above, or a salt thereof, with a compound represented by the formula (II)

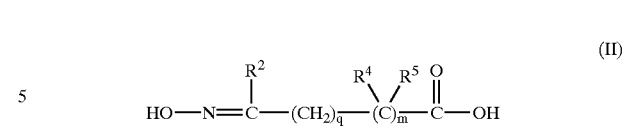

wherein the symbols in the formula are as defined above, or a salt thereof, in an amide in the presence of a metal alkoxide.

2. The production method of claim 1, wherein the metal alkoxide is an alkali metal C$_{1-4}$ alkoxide.

3. The production method of claim 2, wherein the alkali metal C$_{1-4}$ alkoxide is sodium tert-butoxide.

4. The production method of claim 1, wherein the amide is N,N-dimethylacetamide, N,N-dimethylformamide, 1-methyl-2-pyrrolidone or 1,3-dimethyl-2-imidazolidinone.

5. The production method of claim 4, wherein the amide is N,N-dimethylacetamide.

6. The production method of claim 1, wherein the metal alkoxide is sodium tert-butoxide and the amide is N,N-dimethylacetamide.

7. The production method of claim 1, wherein the compound represented by the formula (III) is (E)-4-[4-(5-methyl-2-phenyl-4-oxazolylmethoxy)benzyloxyimino]-4-phenylbutanoic acid or a salt thereof.

8. The production method of claim 1, wherein the compound represented by the formula (III) is (E)-8-[4-(5-methyl-2-phenyl-4-oxazolylmethoxy)benzyloxyimino]-8-phenyloctanoic acid or a salt thereof.

9. A production method of a compound represented by the formula (V)

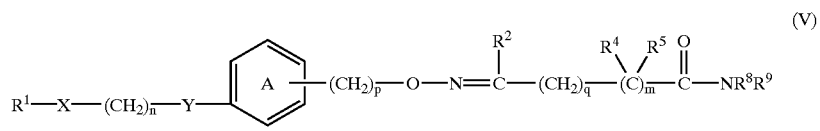

wherein R$^8$ and R$^9$ are the same or different and each is a hydrogen atom, an optionally substituted hydrocarbon group, an optionally substituted heterocyclic group or an optionally substituted acyl group, or R$^8$ and R$^9$ may be bonded to form a ring, and other symbols are as defined in claim 1, or a salt thereof, which comprises amidating the compound represented by the formula (III), which is produced according to the production method in claim 1, or a salt thereof.

10. The production method of claim 9, wherein the compound represented by the formula (V) is (E)-4-[4-(5-methyl-2-phenyl-4-oxazolylmethoxy)benzyloxyimino]-4-phenylbutylamide or a salt thereof.

11. A production method of a compound represented by the formula (V)

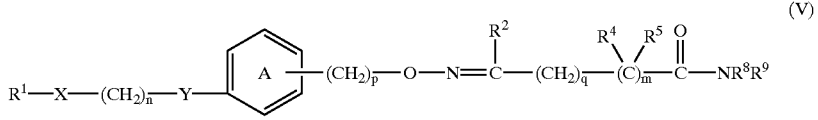
(V)

wherein
- $R^1$ is an optionally substituted hydrocarbon group or an optionally substituted heterocyclic group;
- X is a bond, —CO—, —CH(OH)— or —NR$^6$—($R^6$ is a hydrogen atom or an optionally substituted alkyl group);
- n is an integer of 1 to 3;
- Y is an oxygen atom, a sulfur atom, —SO—, —SO$_2$— or —NR$^7$—($R^7$ is a hydrogen atom or an optionally substituted alkyl group);
- ring A is a benzene ring optionally having 1 to 3 additional substituents;
- p is an integer of 1 to 8;
- $R^2$ is a hydrogen atom or an optionally substituted hydrocarbon group or an optionally substituted heterocyclic group;
- q is an integer of 0 to 6;
- m is 0 or 1;
- $R^6$ and $R^9$ are the same or different and each is a hydrogen atom, an optionally substituted hydrocarbon group, an optionally substituted heterocyclic group, or an optionally substituted acyl group, or $R^8$ and $R^9$ may be bonded to form a ring; and
- $R^4$ and $R^5$ are the same or different and each is a hydrogen atom or an optionally substituted hydrocarbon group, or $R^4$ may be bonded to $R^2$ to form a ring, or a salt thereof, which comprises reacting a compound represented by the formula (I)

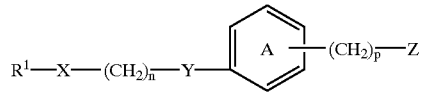
(I)

wherein Z is a halogen atom or OSO$_2$R$^{10}$ ($R^{10}$ is an alkyl group having 1 to 4 carbon atoms, an aryl group having 6 to 10 carbon atoms which is optionally substituted by alkyl group having 1 to 4 carbon atoms); and other symbols in the formula are as defined above, or a salt thereof, with a compound represented by the formula (IV)

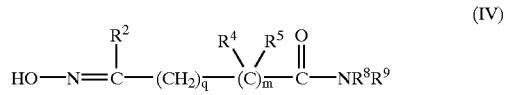
(IV)

wherein each symbol in the formula is as defined above, or a salt thereof, in an amide in the presence of a metal carbonate.

12. The production method of claim 11, wherein the metal carbonate is an alkali metal carbonate.

13. The production method of claim 11, wherein the amide is N,N-dimethylacetamide, N,N-dimethylformamide, 1-methyl-2-pyrrolidone or 1,3-dimethyl-2-imidazolidinone.

14. The production method of claim 11, wherein the compound represented by the formula (V) is (E)-4-[4-(5-methyl-2-phenyl-4-oxazolylmethoxy)benzyloxyimino]-4-phenylbutylamide or a salt thereof.

* * * * *

UNITED STATES PATENT AND TRADEMARK OFFICE
CERTIFICATE OF CORRECTION

PATENT NO.    : 6,518,435 B1
DATED         : February 11, 2003
INVENTOR(S)   : Taihei Yamane et al.

It is certified that error appears in the above-identified patent and that said Letters Patent is hereby corrected as shown below:

Column 29,
Line 63, change "optionally, substituted" to -- optionally substituted --.

Column 31,
Line 31, change "$R^6$" to -- $R^8$ --.

Signed and Sealed this

Third Day of February, 2004

JON W. DUDAS
*Acting Director of the United States Patent and Trademark Office*